(12) United States Patent
Arnin

(10) Patent No.: US 8,870,959 B2
(45) Date of Patent: Oct. 28, 2014

(54) SPINAL FUSION CAGE HAVING POST-OPERATIVE ADJUSTABLE DIMENSIONS

(75) Inventor: Uri Arnin, Kiryat Tivon (IL)

(73) Assignee: Spine21 Ltd., Haifa (IL)

( * ) Notice: Subject to any disclaimer, the term of this patent is extended or adjusted under 35 U.S.C. 154(b) by 34 days.

(21) Appl. No.: 13/511,425

(22) PCT Filed: Nov. 5, 2010

(86) PCT No.: PCT/US2010/055532
§ 371 (c)(1),
(2), (4) Date: May 23, 2012

(87) PCT Pub. No.: WO2011/066077
PCT Pub. Date: Jun. 3, 2011

(65) Prior Publication Data
US 2012/0277875 A1   Nov. 1, 2012

Related U.S. Application Data

(60) Provisional application No. 61/272,959, filed on Nov. 24, 2009.

(51) Int. Cl.
*A61F 2/44* (2006.01)
*A61F 2/30* (2006.01)
*A61F 2/48* (2006.01)

(52) U.S. Cl.
CPC ....... *A61F 2/4455* (2013.01); *A61F 2220/0041* (2013.01); *A61F 2002/30736* (2013.01); *A61F 2002/30553* (2013.01); *A61F 2250/0008* (2013.01); *A61F 2250/0002* (2013.01); *A61F 2002/482* (2013.01); *A61F 2220/0025* (2013.01); *A61F 2250/0009* (2013.01); *A61F 2002/30556* (2013.01); *A61F 2230/0082* (2013.01); *A61F 2002/487* (2013.01); *A61F 2250/0001* (2013.01); *A61F 2002/30401* (2013.01); *A61F 2002/30266* (2013.01); *A61F 2002/3067* (2013.01); *A61F 2002/30398* (2013.01); *A61F 2002/30525* (2013.01); *A61F 2002/30828* (2013.01); *A61F 2002/30527* (2013.01); *A61F 2002/30403* (2013.01); *A61F 2002/30551* (2013.01); *A61F 2002/30668* (2013.01); *A61F 2002/30523* (2013.01); *A61F 2002/485* (2013.01); *A61F 2002/30509* (2013.01); *A61F 2/447* (2013.01); *A61F 2002/3093* (2013.01); *A61F 2002/30433* (2013.01); *A61F 2002/30515* (2013.01)
USPC .......... 623/17.11; 623/17.15; 623/17.16

(58) Field of Classification Search
USPC .......... 606/246–249; 623/17.11–17.16
See application file for complete search history.

(56) References Cited

U.S. PATENT DOCUMENTS 5,865,848 A      2/1999   Baker
2005/0060036 A1* 3/2005   Schultz et al. ............. 623/17.15

(Continued)

FOREIGN PATENT DOCUMENTS

EP           1634549         3/2006

OTHER PUBLICATIONS

PCT Search PCT/US2010/055532.

*Primary Examiner* — Pedro Philogene
*Assistant Examiner* — Christina Negrellirodrigue
(74) *Attorney, Agent, or Firm* — Dekel Patent Ltd.; David Klein

(57) ABSTRACT

A spinal implant including first spinal attachment member for attaching to a first spinal portion, second spinal attachment member for attaching to a second spinal portion, and a post-implantation variable dimension device disposed between the first and second spinal attachment members, which is operable after completing surgery in which said spinal implant was installed into a patient, to cause relative movement between the first and second spinal attachment members.

9 Claims, 2 Drawing Sheets

(56) References Cited

U.S. PATENT DOCUMENTS

| | | |
|---|---|---|
| 2005/0177235 A1 | 8/2005 | Baynham |
| 2007/0270968 A1* | 11/2007 | Baynham et al. .......... 623/17.11 |
| 2008/0033440 A1* | 2/2008 | Moskowitz et al. ............ 606/72 |
| 2009/0125062 A1* | 5/2009 | Arnin ............................ 606/246 |

* cited by examiner

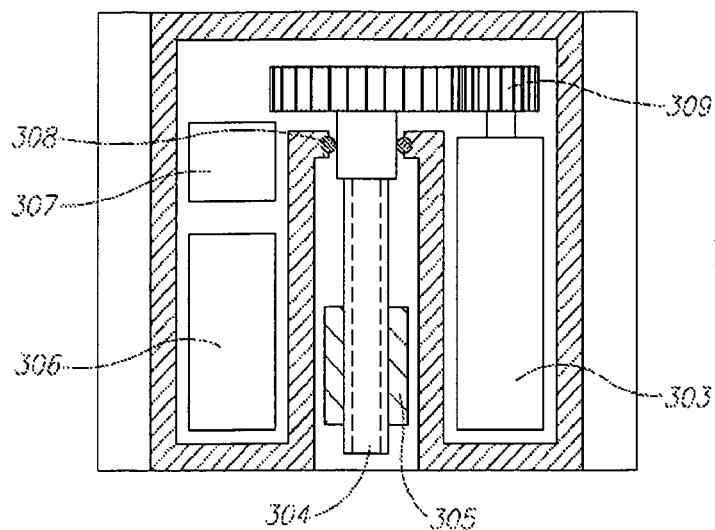
FIG. 4
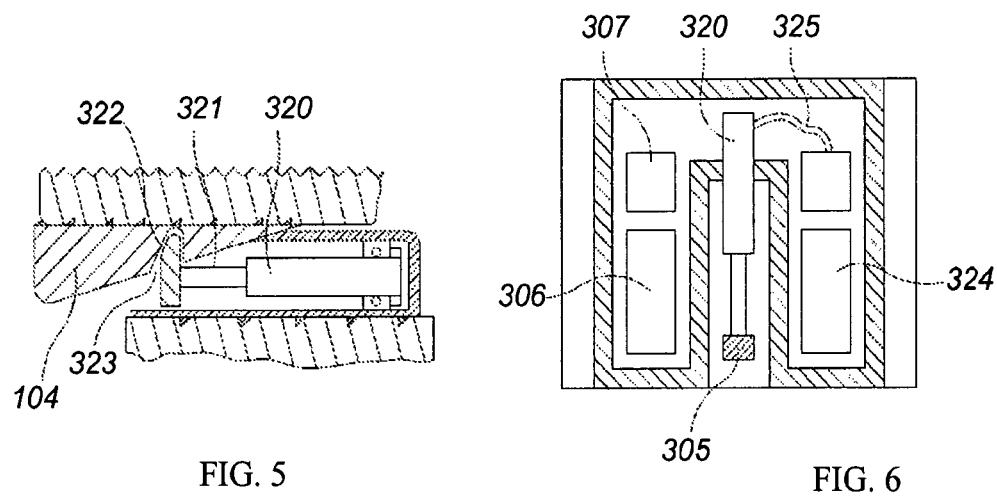
FIG. 5
FIG. 6

SPINAL FUSION CAGE HAVING POST-OPERATIVE ADJUSTABLE DIMENSIONS

CROSS REFERENCE TO OTHER APPLICATIONS

This application is a U.S. national phase application of PCT patent application PCT/US2010/055532, filed Nov. 5, 2010, which claims priority from U.S. Provisional Patent Application 61/272,959, filed Nov. 24, 2009.

FIELD OF THE INVENTION

The present invention relates generally to spinal implants and prostheses, and particularly to a spinal fusion cage having post-operative adjustable dimensions.

BACKGROUND OF THE INVENTION

Spinal implants with the capability of height adjustment are known. One device is shown and described in PCT Patent Application PCT/IL2008/001423 (WO 2009/060427), to the present applicant. One of the devices shown therein uses an inclined, threaded interface between first and second support plates, as is now described with reference to FIG. 1.

The prior art device is a spinal implant 50 that includes a post-implantation variable dimension device 52, used to change the location of adjacent vertebrae 51 and 53. Spinal implant 50 includes a first (upper) support plate 54 having a threaded slot in which a threaded screw 55 is threadedly received. Spinal implant 50 includes a second (lower) support plate 56 that includes a recess in which an electrical motor (or actuator) 57 is mounted. The electrical motor 57 (which may be remote controlled) turns screw 55, which causes first support plate 54 to slide with respect to second support plate 56. The inclined mating between first and second support plates (spinal attachment members) 54 and 56 causes a change in the adjacent location between the two vertebras, both in the vertical and the sagittal planes.

SUMMARY OF THE INVENTION

The present invention seeks to provide an improved spinal implant (or prosthesis, the terms being used interchangeably) having post-operative adjustable dimensions, to be placed between two adjacent vertebras, with the ability to adjust both the height between the vertebras and also the sagittal position of one in respect to the other. In contradistinction to the above prior art, in the present invention, the inclined interface is not threaded; rather the vertebral attachment members slide over each other by means of inclined alignment rails.

In one embodiment, at least one of the dimensions of the spinal implant can be modified post-implantation by means of remote control. The adjustable mechanism (also referred to as a variable dimension mechanism) can have an inclined alignment rail. The adjustment of the height and sagittal location of the parts of the cage, in respect to each other, can be electrically powered, such as by an electric motor (powered by a battery or remote induction), and controlled via remote control.

The prosthesis is configured to bridge between two vertebrae, most preferably but not limited to, adjacent vertebrae. The prosthesis includes a plurality of attachment members (end features) configured to be attached to a plurality of bone attachment points, such as but not limited to, vertebral end plates.

There is thus provided in accordance with a non-limiting embodiment of the present invention a spinal implant including first spinal attachment member for attaching to a first spinal portion, second spinal attachment member for attaching to a second spinal portion, and a post-implantation variable dimension device disposed between the first and second spinal attachment members, which is operable after completing surgery in which said spinal implant was installed into a patient, to cause relative movement between the first and second spinal attachment members.

In accordance with an embodiment of the present invention the first and second spinal attachment members include an inclined alignment rail.

In accordance with an embodiment of the present invention the post-implantation variable dimension device changes a distance between the first and second spinal attachment members.

In accordance with an embodiment of the present invention the post-implantation variable dimension device changes a location of the first and second spinal attachment members both in vertical and sagittal planes.

In accordance with an embodiment of the present invention the first spinal attachment members include a slot (channel) and a pulling element disposed in this slot pulls or pushes this first attachment member in respect to the second attachment member.

In accordance with an embodiment of the present invention the pulling element is actuated by a threaded shaft which is turned by a gear train, wherein rotation of the gear train changes the distance between the first and second support plates.

In accordance with an embodiment of the present invention the first and second spinal attachment members include first and second alignment rails inclined with respect to each other.

In accordance with an embodiment of the present invention the post-implantation variable dimension device is hydraulically or pneumatically operated.

In accordance with an embodiment of the present invention the post-implantation variable dimension device is electrically operated.

In accordance with an embodiment of the present invention the post-implantation variable dimension device includes an internal, implanted portion. The internal portion may include at least one of a piston, a pump, a microprocessor, an RF emitter/transmitter, an LVDT (linear variable differential transducer), a strain sensor, an electric coil, a battery, and a capacitor.

In accordance with an embodiment of the present invention the post-implantation variable dimension device includes an external control portion. The external control portion may include at least one of a control panel, a processor, an RF transmitter/emitter, a magnetic power source, an electric coil and a cellular communication device. The communication between the external control portion and the implanted portion may be controlled by a code or password to protect against undesired operation of the internal device.

BRIEF DESCRIPTION OF THE DRAWINGS

The present invention will be understood and appreciated more fully from the following detailed description, taken in conjunction with the drawings in which:

FIG. 4 is a simplified illustration of a spinal implant including a post-implantation variable dimension device, constructed and operative in accordance with another embodiment of the invention;

FIG. 5 is a simplified illustration of a spinal implant including a post-implantation variable dimension device constructed and operative in accordance with still another embodiment of the present invention; and FIG. 6 is a simplified illustration of a fluid-actuated piston in the configuration of the embodiment of FIG. 4.

DETAILED DESCRIPTION OF EMBODIMENTS

Figure 1:
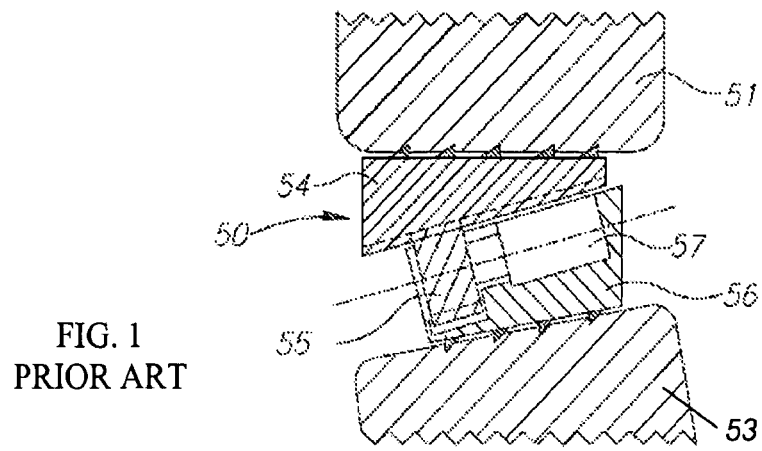
FIG. 1 is a simplified pictorial illustration of a spinal implant including a post-implantation variable dimension device of the prior art.
Figure 2:
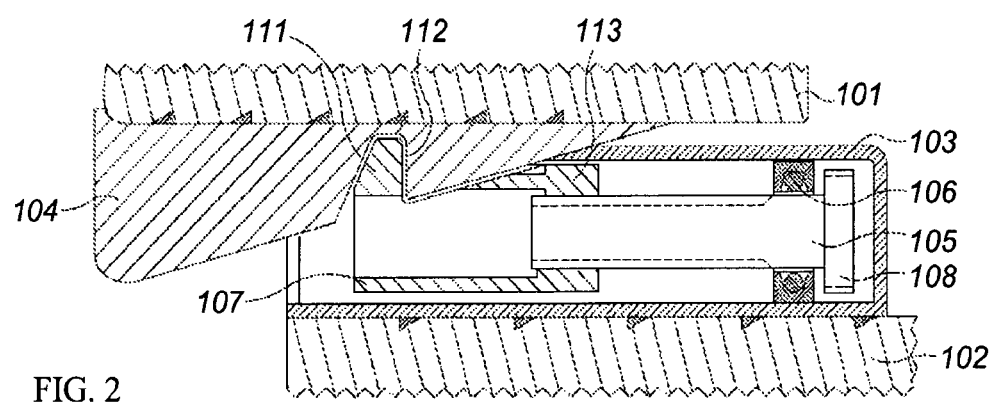
FIG. 2 is a simplified, partially cross-sectional illustration of a spinal implant including a post-implantation variable dimension device, constructed and operative in accordance with an embodiment of the invention.

Reference is now made to FIG. 2, which illustrates a spinal implant 100, constructed and operative in accordance with a non-limiting embodiment of the invention.

Figure 3:
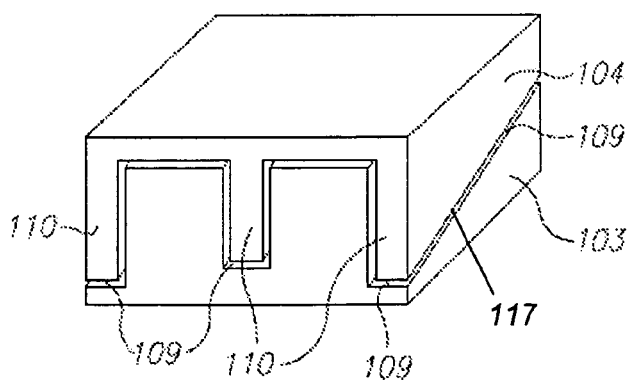
FIG. 3 is a simplified pictorial illustration of inclined alignment rails of the device of FIG. 2, in accordance with an embodiment of the invention.

Spinal implant 100 is shown implanted between two adjacent vertebras 101 and 102. Spinal implant 100 includes a first (e.g., upper) spinal attachment member 104 arranged for sliding over a second (e.g., lower) spinal attachment member 103. More specifically, first and second attachment members 104 and 103 include at least one inclined alignment rail 110 that slides over at least one inclined channel 109 (the rail or rails are formed in one of the attachment members and the channel or channels are formed in the other attachment member). (The rails and channels are not visible in the section of FIG. 2, but an example of them is shown in FIG. 3). The first attachment member 104 slides over the second attachment member 103 by being pulled or pushed by a pulling element 107. The first and second attachment members 104 and 103 form a spinal fusion cage having post-operative adjustable dimensions.

Surfaces of the attachment members in contact with bone may be coated to promote osseous integration.

In accordance with a non-limiting embodiment of the invention, pulling element 107 includes a distal tongue 111 that is received in a recess 112 formed in first attachment member 104. A proximal end 113 of pulling element 107 is internally threaded to mate with a threaded rod 105 (also called screw 105). First attachment member 104 is sufficiently hollow to allow threaded rod 105 to enter and advance into first attachment member 104.

The threaded rod 105 can be rotated by a gear system 108, actuated by a gear train powered by an actuating motor, not shown here but shown in FIG. 4. A seal 106 can be disposed between components located in a closed compartment and elements exposed to the human body.

In accordance with a non-limiting embodiment of the present invention, pulling element 107 and threaded rod 105 are disposed completely or partially in attachment member 103. A bearing element, such as any kind of bearing, lubrication, surface treatment and the like, can be used to reduce the friction between the pulling element 107 and/or threaded rod 105 and attachment members 103 and/or 104.

In accordance with an embodiment of the present invention the gear system 108 can be spur gear, worm gear, belt, chain or other known mechanisms to transmit motion.

Reference is now made to FIG. 3, which illustrates inclined alignment rails 110, in accordance with a non-limiting embodiment of the invention. The alignment rails 110 can have a predesigned angle to create different relations between the sagittal and the vertical translations. The at least one alignment rail 110 can be located symmetrically about the center of the device or not symmetrically about the center (e.g., off-center). The sliding surface of channels 109 may include a bearing element 117, such as any kind of bearing, lubrication, surface treatment and the like, to reduce friction.

The illustrated embodiment shows the at least one alignment rail 110 with a generally rectangular shape; however, different contours can be used as well to carry out the invention, such as but not including, dove tail, rounded shape, T shape or any other shapes.

Reference is now made to FIG. 4, which illustrates a cross section of a spinal implant including a post-implantation variable dimension device constructed and operative in accordance with an embodiment of the present invention.

A pulling element 305 is pulled by a threaded rod 304. Threaded rod 304 is connected to a gear train 309, powered by an actuating motor 303. A battery 306 and a printed circuit 307 are used to control the motor 303. A seal 308 is used to separate between encapsulated elements and the human body, not shown.

In accordance with an embodiment of the present invention, printed circuit 307 can include at least one of a micro-controller, a radio system, a remote switch, a capacitor, and an induction coil. The electrical components may be controlled by an external unit via remote control (radio, light, voice etc). Instead of being electrically actuated, actuating motor 303 can be hydraulic or pneumatic.

Reference is now made to FIG. 5, which illustrates a cross section of a spinal implant including a post-implantation variable dimension device constructed and operative in accordance with another embodiment of the present invention. In this embodiment, the pulling element includes a piston 320 with a rod 321. A tongue 322 at a distal end of rod 321 is received in a recess 323 formed in first attachment member 104. Piston 320 may be electrically, pneumatically or hydraulically (i.e., fluidly) operated.

FIG. 6 illustrates an example of a hydraulic or pneumatic piston 320 in the configuration of the embodiment of FIG. 4. The pulling element 305 is at the distal end of rod 321. Piston 320 is operated by a pneumatic or hydraulic (i.e., fluid) pump 324, connected thereto by a tube 325.

The embodiments of FIGS. 2-6 can be interchanged and/or integrated with one another in different combinations.

What is claimed is:

1. A spinal implant characterised by:
   first and second spinal attachment members that comprise at least one inclined alignment rail that slides over at least one inclined channel; and
   a pulling element arranged to cause said first and second spinal attachment members to slide relative to one another via said at least one inclined alignment rail and said at least one inclined channel;
   wherein a proximal end of said pulling element is internally threaded and mates with a threaded rod, and said threaded rod is rotated by a gear system powered by an actuating motor, and said actuating motor is controlled by a printed circuit, which comprises at least one of a micro-controller, a radio system, a remote switch, a capacitor, and an induction coil.

2. The spinal implant according to claim 1, wherein said pulling element comprises a distal tongue that is received in a recess formed in said first attachment member.

3. The spinal implant according to claim 1, wherein said at least one alignment rail has a predesigned angle to create different relations between sagittal and vertical translations of said first and second spinal attachment members when sliding relative to one another.

4. The spinal implant according to claim 1, wherein said least one alignment rail is located symmetrically about a center of said implant.

5. The spinal implant according to claim 1, wherein said least one alignment rail is not located symmetrically about a center of said implant.

6. The spinal implant according to claim 1, wherein surfaces of said first and second spinal attachment members in contact with bone are coated to promote osseous integration.

7. The spinal implant according to claim 1, wherein a sliding surface of said channels comprises a bearing element.

8. The spinal implant according to claim 1, wherein said pulling element is moved by a piston with a rod.

9. The spinal implant according to claim 8, wherein said piston is a fluid-actuated piston connected to a fluid pump by a tube.

* * * * *